United States Patent
Shen et al.

(10) Patent No.: US 12,116,422 B2
(45) Date of Patent: Oct. 15, 2024

(54) STAPLED PEPTIDE AND USE THEREOF IN PREPARATION OF DRUG FOR TREATING PANCREATIC CANCER

(71) Applicant: Ruijin Hospital, Shanghai Jiao Tong University School of Medicine, Shanghai (CN)

(72) Inventors: Baiyong Shen, Shanghai (CN); Shuyu Zhai, Shanghai (CN); Da Fu, Shanghai (CN); Xiaxing Deng, Shanghai (CN); Xiaomei Tang, Shanghai (CN)

(73) Assignee: Ruijin Hospital, Shanghai Jiao Tong University School of Medicine, Shanghai (CN)

( * ) Notice: Subject to any disclaimer, the term of this patent is extended or adjusted under 35 U.S.C. 154(b) by 102 days.

(21) Appl. No.: 18/064,719

(22) Filed: Dec. 12, 2022

(65) Prior Publication Data
US 2023/0416305 A1 Dec. 28, 2023

(30) Foreign Application Priority Data
Jun. 27, 2022 (CN) .......................... 202210733001.1

(51) Int. Cl.
C07K 7/08 (2006.01)
A61K 38/00 (2006.01)
A61P 35/00 (2006.01)

(52) U.S. Cl.
CPC ................ *C07K 7/08* (2013.01); *A61P 35/00* (2018.01); *A61K 38/00* (2013.01)

(58) Field of Classification Search
None
See application file for complete search history.

(56) References Cited

PUBLICATIONS

Wallensky L and Bird G "Hydrocarbon-Stapled Peptides; Principles, Practice, and Progress" J. Med. Chem. 57:6275-6288. (Year: 2014).*

Zhai et al. "A microprotein N1DARP encoded by LINC00261 promotes Notch1 intracellular domain (N1ICD) degradation via disrupting UPS10-N1ICD interaction to inhibit chemoresistance in Notch1-hyperactivated pancreatic cancer" Cell Discovery 9:95. (Year: 2023).*

* cited by examiner

*Primary Examiner* — Sudhakar Katakam
*Assistant Examiner* — Zachary J Miknis
(74) *Attorney, Agent, or Firm* — Amster, Rothstein & Ebenstein LLP

(57) ABSTRACT

The present disclosure provides a stapled peptide and use thereof in preparation of a drug for treating pancreatic cancer, belonging to the technical field of biomedicine. The stapled peptide is prepared by using a linear peptide with an amino acid sequence shown in SEQ ID NO: 1 as a peptide chain template, and replacing i-th and (i+7)-th amino acids of the linear peptide with S5 separately and conducting cyclization; alternatively, replacing n-th and (n+4)-th amino acids of the linear peptide with S5 separately and conducting cyclization; where S5 is 2-amino-2-methyl-6-heptenoic acid; i is a positive integer of less than or equal to 7, and n is a positive integer of less than or equal to 10. The stapled peptide treats LINC00261-deficient pancreatic cancer, N1DARP-deficient pancreatic cancer, or gemcitabine-resistant pancreatic cancer by specifically inhibiting a deubiquitination activity of USP10.

20 Claims, 18 Drawing Sheets
Specification includes a Sequence Listing.

C

| SAH peptide | Sequence | KD (M) |
|---|---|---|
| mAH2 | YAKRIFYQLLSKQL | $6.04 \times 10^{-8}$ |
| SAH-mAH2-1 | S₅AKRS₅FYQLLSKQL | $1.34 \times 10^{-7}$ |
| SAH-mAH2-2 | YS₅KRIS₅YQLLSKQL | $9.77 \times 10^{-8}$ |
| SAH-mAH2-3 | YAKRIS₅YQLS₅SKQL | $1.05 \times 10^{-9}$ |
| SAH-mAH2-4 | S₅AKRIFYS₅LLSKQL | $2.58 \times 10^{-8}$ |
| SAH-mAH2-5 | YAKRIS₅YQLLSKS₅L | $8.98 \times 10^{-10}$ |

| Mutation | Mutated position | KD (M) |
|---|---|---|
| AH2 | YAKRIFYQLLSKEL | 6.04E-08 |
| mAH2 | YAKRIFYQLLSKQL | 4.52E-08 |
| mAH2-1 | AAKRIFYQLLSKQL | 9.61E-08 |
| mAH2-3 | YAARIFYQLLSKQL | 5.11E-08 |
| mAH2-4 | YAKAIFYQLLSKQL | 7.45E-08 |
| mAH2-5 | YAKRAFYQLLSKQL | 5.75E-08 |
| mAH2-6 | YAKRIAYQLLSKQL | 6.36E-08 |
| mAH2-7 | YAKRIFAQLLSKQL | / |
| mAH2-8 | YAKRIFYALLSKQL | 8.74E-08 |
| mAH2-9 | YAKRIFYQALSKQL | 2.86E-07 |
| mAH2-10 | YAKRIFYQLASKQL | 5.55E-08 |
| mAH2-11 | YAKRIFYQLLAKQL | 8.39E-08 |
| mAH2-12 | YAKRIFYQLLSAQL | 7.82E-08 |
| mAH2-13 | YAKRIFYQLLSKAL | 9.90E-08 |
| mAH2-14 | YAKRIFYQLLSKQA | 5.98E-06 |

FIG. 1D

SEQUENCE LISTING

```
Sequence total quantity: 22
SEQ ID NO: 1          moltype = AA  length = 14
FEATURE               Location/Qualifiers
source                1..14
                      mol_type = protein
                      note = mAH2
                      organism = synthetic construct
```

```
SEQUENCE: 1
YAKRIFYQLL SKQL                                                              14

SEQ ID NO: 2            moltype = AA  length = 41
FEATURE                 Location/Qualifiers
source                  1..41
                        mol_type = protein
                        note = N1DARP
                        organism = synthetic construct
SEQUENCE: 2
MVLLEKKRQY QGLCLLSPGY AKRIFYQLLS KELYVDPIHI D                                 41

SEQ ID NO: 3            moltype = AA  length = 8
FEATURE                 Location/Qualifiers
source                  1..8
                        mol_type = protein
                        note = AH1
                        organism = synthetic construct
SEQUENCE: 3
LLEKKRQY                                                                     8

SEQ ID NO: 4            moltype = AA  length = 14
FEATURE                 Location/Qualifiers
source                  1..14
                        mol_type = protein
                        note = AH2
                        organism = synthetic construct
SEQUENCE: 4
YAKRIFYQLL SKEL                                                              14

SEQ ID NO: 5            moltype = AA  length = 14
FEATURE                 Location/Qualifiers
source                  1..14
                        mol_type = protein
                        note = SAH-mAH2-1
                        organism = synthetic construct
SITE                    1
                        note = 2-amino-2-methyl-6-heptenoic acid
SITE                    5
                        note = 2-amino-2-methyl-6-heptenoic acid
SEQUENCE: 5
XAKRXFYQLL SKQL                                                              14

SEQ ID NO: 6            moltype = AA  length = 14
FEATURE                 Location/Qualifiers
source                  1..14
                        mol_type = protein
                        note = SAH-mAH2-2
                        organism = synthetic construct
SITE                    2
                        note = 2-amino-2-methyl-6-heptenoic acid
SITE                    6
                        note = 2-amino-2-methyl-6-heptenoic acid
SEQUENCE: 6
YXKRIXYQLL SKQL                                                              14

SEQ ID NO: 7            moltype = AA  length = 13
FEATURE                 Location/Qualifiers
source                  1..13
                        mol_type = protein
                        note = SAH-mAH2-3
                        organism = synthetic construct
SITE                    10
                        note = 2-amino-2-methyl-6-heptenoic acid
SITE                    6
                        note = 2-amino-2-methyl-6-heptenoic acid
SEQUENCE: 7
YAKRIXYQLX KQL                                                               13

SEQ ID NO: 8            moltype = AA  length = 14
FEATURE                 Location/Qualifiers
source                  1..14
                        mol_type = protein
                        note = SAH-mAH2-4
                        organism = synthetic construct
SITE                    1
                        note = 2-amino-2-methyl-6-heptenoic acid
SITE                    8
                        note = 2-amino-2-methyl-6-heptenoic acid
```

-continued

```
SEQUENCE: 8
XAKRIFYXLL SKQL                                                              14

SEQ ID NO: 9            moltype = AA   length = 14
FEATURE                 Location/Qualifiers
source                  1..14
                        mol_type = protein
                        note = SAH-mAH2-5
                        organism = synthetic construct
SITE                    6
                        note = 2-amino-2-methyl-6-heptenoic acid
SITE                    13
                        note = 2-amino-2-methyl-6-heptenoic acid
SEQUENCE: 9
YAKRIXYQLL SKXL                                                              14

SEQ ID NO: 10           moltype = AA   length = 14
FEATURE                 Location/Qualifiers
source                  1..14
                        mol_type = protein
                        note = mAH2-1
                        organism = synthetic construct
SEQUENCE: 10
AAKRIFYQLL SKQL                                                              14

SEQ ID NO: 11           moltype = AA   length = 14
FEATURE                 Location/Qualifiers
source                  1..14
                        mol_type = protein
                        note = mAH2-3
                        organism = synthetic construct
SEQUENCE: 11
YAARIFYQLL SKQL                                                              14

SEQ ID NO: 12           moltype = AA   length = 14
FEATURE                 Location/Qualifiers
source                  1..14
                        mol_type = protein
                        note = mAH2-4
                        organism = synthetic construct
SEQUENCE: 12
YAKAIFYQLL SKQL                                                              14

SEQ ID NO: 13           moltype = AA   length = 14
FEATURE                 Location/Qualifiers
source                  1..14
                        mol_type = protein
                        note = mAH2-5
                        organism = unidentified
SEQUENCE: 13
YAKRAFYQLL SKQL                                                              14

SEQ ID NO: 14           moltype = AA   length = 14
FEATURE                 Location/Qualifiers
source                  1..14
                        mol_type = protein
                        note = mAH2-6
                        organism = synthetic construct
SEQUENCE: 14
YAKRIAYQLL SKQL                                                              14

SEQ ID NO: 15           moltype = AA   length = 14
FEATURE                 Location/Qualifiers
source                  1..14
                        mol_type = protein
                        note = mAH2-7
                        organism = synthetic construct
SEQUENCE: 15
YAKRIFAQLL SKQL                                                              14

SEQ ID NO: 16           moltype = AA   length = 14
FEATURE                 Location/Qualifiers
source                  1..14
                        mol_type = protein
                        note = mAH2-8
                        organism = synthetic construct
SEQUENCE: 16
YAKRIFYALL SKQL                                                              14
```

```
SEQ ID NO: 17            moltype = AA   length = 14
FEATURE                  Location/Qualifiers
source                   1..14
                         mol_type = protein
                         note = mAH2-9
                         organism = synthetic construct
SEQUENCE: 17
YAKRIFYQAL SKQL                                                              14

SEQ ID NO: 18            moltype = AA   length = 14
FEATURE                  Location/Qualifiers
source                   1..14
                         mol_type = protein
                         note = mAH2-10
                         organism = synthetic construct
SEQUENCE: 18
YAKRIFYQLA SKQL                                                              14

SEQ ID NO: 19            moltype = AA   length = 14
FEATURE                  Location/Qualifiers
source                   1..14
                         mol_type = protein
                         note = mAH2-11
                         organism = synthetic construct
SEQUENCE: 19
YAKRIFYQLL AKQL                                                              14

SEQ ID NO: 20            moltype = AA   length = 14
FEATURE                  Location/Qualifiers
source                   1..14
                         mol_type = protein
                         note = mAH2-12
                         organism = synthetic construct
SEQUENCE: 20
YAKRIFYQLL SAQL                                                              14

SEQ ID NO: 21            moltype = AA   length = 14
FEATURE                  Location/Qualifiers
source                   1..14
                         mol_type = protein
                         note = mAH2-13
                         organism = synthetic construct
SEQUENCE: 21
YAKRIFYQLL SKAL                                                              14

SEQ ID NO: 22            moltype = AA   length = 14
FEATURE                  Location/Qualifiers
source                   1..14
                         mol_type = protein
                         note = mAH2-14
                         organism = synthetic construct
SEQUENCE: 22
YAKRIFYQLL SKQA                                                              14
```

STAPLED PEPTIDE AND USE THEREOF IN PREPARATION OF DRUG FOR TREATING PANCREATIC CANCER

CROSS-REFERENCE TO RELATED APPLICATION

This patent application claims the benefit and priority of Chinese Patent Application No. 202210733001.1, filed with the China National Intellectual Property Administration on Jun. 27, 2022, the disclosure of which is incorporated by reference herein in its entirety as part of the present application.

REFERENCE TO SEQUENCE LISTING

A computer readable XML file entitled "GWP20221000005_sequence_listing_r1.xml", that was created on Dec. 19, 2022, with a file size of about 27,883 bytes, contains the sequence listing for this application, has been filed with this application, and is hereby incorporated by reference in its entirety.

TECHNICAL FIELD

The present disclosure belongs to the technical field of biomedicine, and in particular relates to a stapled peptide and use thereof in preparation of a drug for treating pancreatic cancer.

BACKGROUND

Oncogenes and tumor suppressor genes play an extremely-important role in the occurrence of cancer. Oncogenes, which are mutant forms of normal genes (also called proto-oncogenes) that control the growth and division of cells, can cause normal cells to become cancerous. The proteins encoded by oncogenes mainly include growth factors, growth factor receptors, molecules in signal transduction pathways, gene transcription regulators, and cell cycle regulatory proteins. Tumor suppressor genes are negative regulators in the proliferation of normal cells, and the proteins encoded by the tumor suppressor genes often play a role of preventing cycle progression in cell cycle checkpoints. The occurrence of cancer is the result of accumulation of genetic mutations.

Pancreatic cancer is one of the most malignant digestive tract cancers and has the worst prognosis of all major malignancies, with a 5-year survival rate of not more than 10%. Pancreatic ductal adenocarcinoma (PDAC) accounts for approximately 90% of the diagnosed pancreatic cancer. Only 20% of pancreatic cancer patients are eligible for surgery, while others have no choice but to receive chemotherapy. PDAC is notorious for being refractory and resistant to standard chemotherapy due to its inherent intratumoral heterogeneity and highly-desmoplastic tumor microenvironment. Therefore, targeting key genes of drug resistance may improve chemotherapy resistance to provide an effective way to eradicate pancreatic cancer.

The Notch pathway has been reported to be active in various human cancers, including breast cancer, colorectal cancer, lung cancer, prostate cancer, and glioblastoma, as well as pancreatic cancer. Notch signaling is positively associated with occurrence, progression, and drug resistance of pancreatic tumors in cell lines and mutant mice. Pharmacological inhibition of Notch signaling slows proliferation and invasion, induces intratumoral apoptosis, and enhances chemotherapy in preclinical models. Notch is a relatively short-lived protein that is rapidly degraded mainly by the ubiquitin-proteasome system. Many components are involved in regulating the stability of Notch1 in various cancer types. Studies on the degradation of Notch members have also involved the Notch intracellular domain (NICD), a Notch fragment that is activated and cleaved. NICD translocates to the nucleus as a trans-activator that includes several ankyrin-like repeats (ANKs), a PEST domain, multiple nuclear localization sequences, and a CSL binding site called RAM. In addition to ubiquitination, deubiquitinases (DUBs) that are responsible for the ubiquitin cycle also play an equally important role in regulating Notch degradation. Promoting ubiquitin-mediated degradation of Notch family members may be an alternative and promising strategy to target Notch-activated cancers. Accordingly, there is an urgent need for novel regulators involved in Notch degradation or the protein complexes it forms.

Long non-coding RNAs (lncRNAs) are defined as transcripts containing more than 200 nucleotides and with limited protein-coding capacity. Numerous studies have shown that the lncRNAs are key regulators involved in a variety of biological processes, including immune responses, inflammation, and cancer initiation and progression. Mechanistically, the molecular functions conducted by lncRNAs are generally identified as signaling, decoy, guide, and scaffold.

However, recently accumulating evidence suggests that functional peptides can be encoded by short open reading frames (ORFs) in lncRNAs and play critical roles in occurrence and development of tumors. An oncopeptide encoded by LINC00266-1, a regulatory subunit of the m6A reader IGF2BP1, enhances m6A recognition of target RNAs. Furthermore, the polypeptide encoded by cyclic LINC-PINT inhibits transcriptional elongation in glioblastoma. However, in pancreatic cancer, the functional peptides encoded by lncRNAs and their roles in occurrence and development of tumors have not been reported so far.

SUMMARY

In view of this, a purpose of the present disclosure is to provide a stapled peptide and use thereof in preparation of a drug for treating pancreatic cancer. The stapled peptide can be used to prepare a drug for treating pancreatic cancer.

The present disclosure provides a stapled peptide, prepared by using a linear peptide with an amino acid sequence shown in SEQ ID NO: 1 as a peptide chain template, and replacing i-th and (i+7)-th amino acids of the linear peptide with S5 separately and conducting cyclization; alternatively, replacing n-th and (n+4)-th amino acids of the linear peptide with S5 separately and conducting cyclization; where S5 is 2-amino-2-methyl-6-heptenoic acid; i is a positive integer of less than or equal to 7, and n is a positive integer of less than or equal to 10.

Preferably, i is 1 or 6.

Preferably, n is 1, 2, or 6.

The present disclosure further provides use of the stapled peptide in preparation of a drug for treating pancreatic cancer.

Preferably, the pancreatic cancer includes LINC00261-deficient pancreatic cancer, N1DARP-deficient pancreatic cancer, or gemcitabine-resistant pancreatic cancer.

The present disclosure further provides a drug for treating pancreatic cancer, including the stapled peptide as an active component, and a pharmaceutically acceptable auxiliary material.

Preferably, the stapled peptide is the only active component of the drug.

Preferably, a dosage form of the drug includes an injection.

The present disclosure provides a stapled peptide, prepared by using a linear peptide with an amino acid sequence shown in SEQ ID NO: 1 as a peptide chain template, and replacing i-th and (i+7)-th amino acids of the linear peptide with S5 separately and conducting cyclization; alternatively, replacing n-th and (n+4)-th amino acids of the linear peptide with S5 separately and conducting cyclization; where S5 is 2-amino-2-methyl-6-heptenoic acid; i is a positive integer of less than or equal to 7, and n is a positive integer of less than or equal to 10. In the present disclosure, the stapled peptide achieves treating LINC00261-deficient pancreatic cancer, N1DARP-deficient pancreatic cancer, or GEM-resistant pancreatic cancer by specifically inhibiting the deubiquitination activity of USP10. Specific inhibition of Notch signaling pathway leads to persistent tumor regression of the LINC00261-deficient pancreatic cancer, N1DARP-deficient pancreatic cancer, or GEM-resistant pancreatic cancer in cell line-, cell-, and pancreatic cancer patient-derived organoids, as well as subcutaneous and orthotopic tumor-bearing mice, without affecting the liver, lungs, and kidneys and other major normal tissues and organs. The stapled peptide shows a potential in the treatment of pancreatic cancer, and provide a reference for the Notch signaling pathway to be a target for precise and individualized treatment of pancreatic cancer.

BRIEF DESCRIPTION OF THE DRAWINGS

FIG. 1A-E show design and optimization of a stapled peptide SAH-mAH that mimics N1DARP; where FIG. 1A shows the prediction of tertiary and secondary structures of N1DARP by an I-TASSAR online prediction tool (http://zhanglab.ccmb.med.umich.edu/I-TASSER/), as well as the affinity of two α-helices (AH1 (SEQ ID NO: 3) and AH2 (SEQ ID NO:4)) to an ANK domain measured by surface plasmon resonance (SPR); FIG. 1B shows that six α-helical regions containing the ANK domain are obtained from a PDB database, and affinity of the six α-helical regions with AH2 is detected by SPR; and SPR detects the substitution affinity of the ANK domain modified with AH2 (mAH2) for each amino acid of Ala; FIG. 1C shows a schematic diagram of S5 replacing amino acids in the mAH2 (namely, SAH-mAH2-1 to SAH-mAH2-5, with the amino acid sequence set forth in SEQ ID NOS: 5-9, respectively) to generate a stitched peptide; FIG. 1D shows the affinity of SAH-mAH2-5 and its analogous stapled peptides (namely mAH2-1 and mAH2-3 to mAH2-14, with the amino acid sequence set forth in SEQ ID NOS: 10-22, respectively) to the ANK domain detected by SPR; and FIG. 1E shows a simulation of molecular docking by ClusPro 2.0, which is demonstrated by PyMOL, showing that the SAH-mAH2-5 is embedded in surface grooves of the ANK through electrostatic attraction, hydrogen bonding, and proper conformation; and data are expressed as mean±SD of three independent experiments;

FIG. 2A shows a schematic diagram of generating four PDOs and a nude mouse PDOX; FIG. 2B shows protein expression levels of USP10 and N1ICD in the four PDOs detected by Western blot; FIG. 2C to FIG. 2F show organoid sizes of the four PDOs treated with a control group (SAH-CTRL) or different concentrations of the SAH-mAH2-5 measured by vernier calipers; FIG. 2G to FIG. 2H show the orthotopic tumor volume and survival analysis of the PDOX model treated with SAH-CTRL or SAH-mAH2-5 at different concentrations; FIG. 2I to FIG. 2K shows calcein AM/PI staining (FIG. 2I), organoid area (FIG. 2J), and apoptosis (FIG. 2K) of anti-GEM organoids cultured with GEM or SAH-mAH2-5 or a combination thereof, which are measured by fluorescence microscopy; and FIG. 2L and FIG. 2M respectively show the orthotopic tumor volume and survival analysis of the PDOX model treated with GEM or SAH-mAH2-5 or a combination thereof after implantation of orthotopic tumors in the PDOX model; data are expressed as mean±SD of three independent experiments, *$P<0.05$, $P<0.01$, *$P<0.001$, and ****$P<0.0001$; ns: no significance;

FIG. 3A shows an influence of the SAH-mAH2-5 on USP10-N1ICD interaction detected by Western blot in pancreatic cancer Capan1 cells; FIG. 3B shows N1ICD remaining at indicated times detected by Western blot in Capan1 incubated with SAH-CTRL or SAH-mAH2-5 after treatment by cycloheximide (CHX); FIG. 3C shows a total ubiquitination level of the N1ICD detected by Western blot using the Capan1 incubated with SAH-CTRL or SAH-mAH2-5; FIG. 4A shows concentrations of alanine aminotransferase (ALT), aspartate aminotransferase (AST), blood urea nitrogen (BUN), and creatinine (CRE) in serum of mice treated with SAH-CTRL or SAH-mAH2-5; and FIG. 4B shows results of HE staining on pancreas, liver, kidney, spleen, lung, and colon of the mice treated with SAH-CTRL or SAH-mAH2-5; ns: no significance.

DETAILED DESCRIPTION OF THE EMBODIMENTS

Figure 1A:
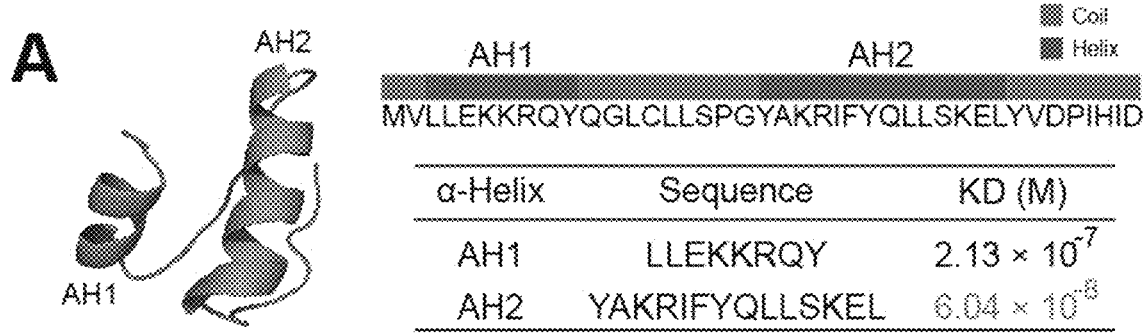

The present disclosure provides a stapled peptide, prepared by using a linear peptide with an amino acid sequence shown in SEQ ID NO: 1 as a peptide chain template, and replacing i-th and (i+7)-th amino acids of the linear peptide with S5 separately and conducting cyclization; alternatively, replacing n-th and (n+4)-th amino acids of the linear peptide with S5 separately and conducting cyclization; where S5 is 2-amino-2-methyl-6-heptenoic acid; i is a positive integer of less than or equal to 7, and n is a positive integer of less than or equal to 10.

In the present disclosure, i is preferably 1 or 6.

In the present disclosure, n is preferably 1, 2, or 6.

In the present disclosure, the linear peptide shown in SEQ ID NO: 1 is named modified AH2 (mAH2), which is a modified α-helice 2 with an amino acid sequence of YAKRIFYQLLSKQL.

In the present disclosure, a stapled peptide whose n is 1 is named SAH-mAH2-1, which has an amino acid structure shown in formula I:
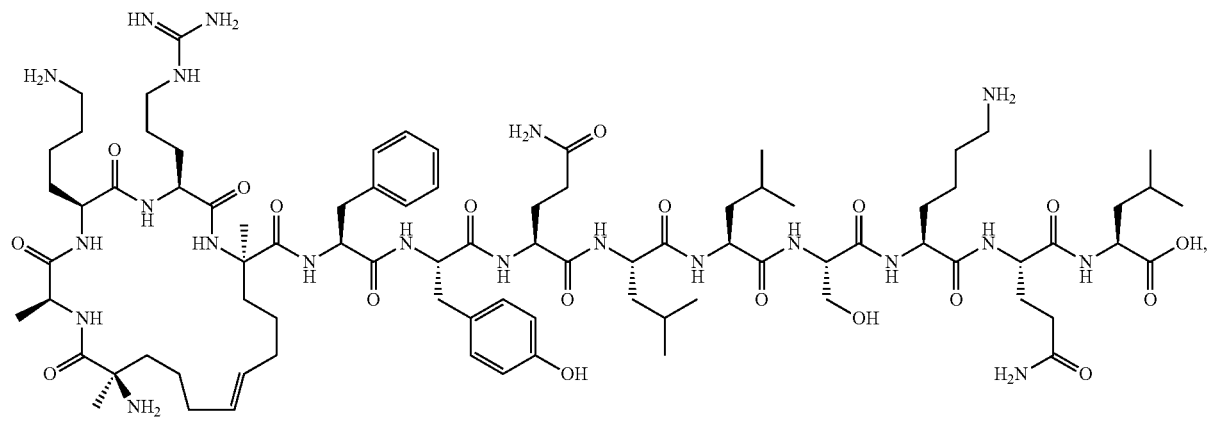 [SMILES: CC(C)C[C@H](NC(=O)[C@H](CCC(N)=O)NC(=O)[C@H](CCCCN)NC(=O)[C@H](CO)NC(=O)[C@H](CC(C)C)NC(=O)[C@H](CC(C)C)NC(=O)[C@H](CCC(N)=O)NC(=O)[C@H](Cc1ccc(O)cc1)NC(=O)[C@H](Cc1ccccc1)NC(=O)[C@@]1(C)CCC/C=C/CCC[C@@](C)(N)C(=O)N[C@@H](C)C(=O)N[C@@H](CCCCN)C(=O)N[C@@H](CCCNC(=N)N)C(=O)N1)C(=O)O]
a chemical formula of $C_{84}H_{137}N_{21}O_{19}$, and a molecular weight of 1745.15 kDa.
In the present disclosure, a stapled peptide whose n is 2 is named SAH-mAH2-2, which has an amino acid structure shown in formula II:
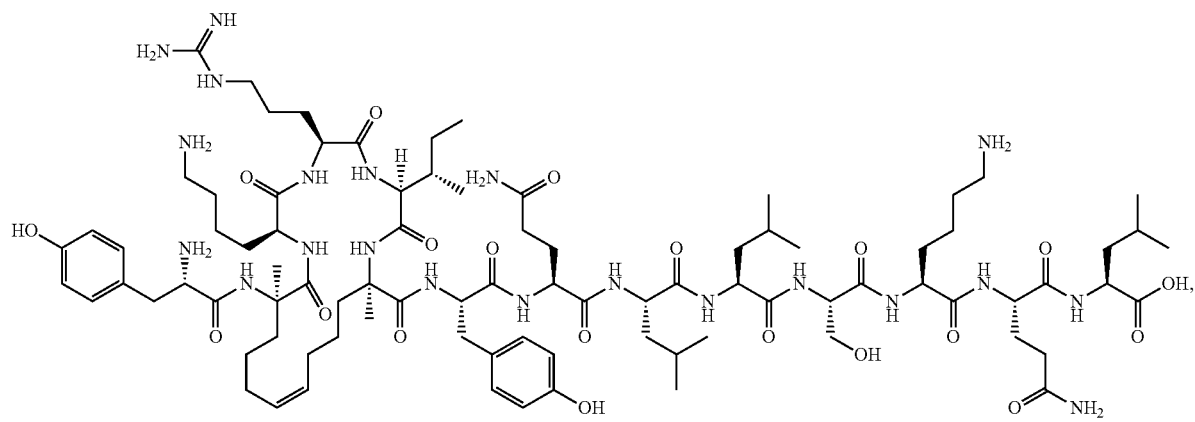 [SMILES: CC[C@H](C)[C@@H]1NC(=O)[C@H](CCCNC(=N)N)NC(=O)[C@H](CCCCN)NC(=O)[C@](C)(NC(=O)[C@@H](N)Cc2ccc(O)cc2)CCC/C=C\CCC[C@](C)(C(=O)N[C@@H](Cc2ccc(O)cc2)C(=O)N[C@@H](CCC(N)=O)C(=O)N[C@@H](CC(C)C)C(=O)N[C@@H](CC(C)C)C(=O)N[C@@H](CO)C(=O)N[C@@H](CCCCN)C(=O)N[C@@H](CCC(N)=O)C(=O)N[C@@H](CC(C)C)C(=O)O)NC1=O]
a chemical formula of $C_{84}H_{143}N_{21}O_{20}$, and a molecular weight of 1803.23 kDa.

In the present disclosure, a stapled peptide whose n is 6 is named SAH-mAH2-3, which has an amino acid structure shown in formula III:

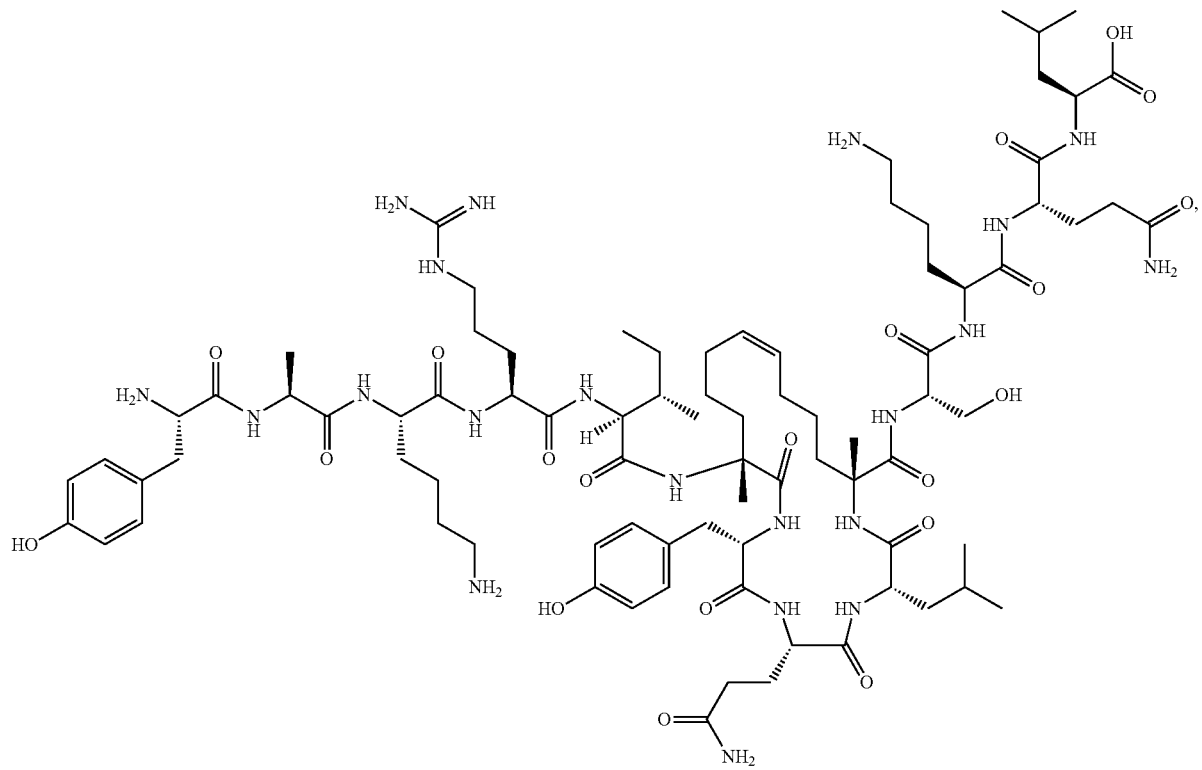 [SMILES: CC[C@H](C)[C@H](NC(=O)[C@H](CCCNC(=N)N)NC(=O)[C@H](CCCCN)NC(=O)[C@H](C)NC(=O)[C@@H](N)Cc1ccc(O)cc1)C(=O)N[C@]1(C)CCC/C=C\CCC[C@](C)(C(=O)N[C@@H](CO)C(=O)N[C@@H](CCCCN)C(=O)N[C@@H](CCC(N)=O)C(=O)N[C@@H](CC(C)C)C(=O)O)NC(=O)[C@H](CC(C)C)NC(=O)[C@H](CCC(N)=O)NC(=O)[C@H](Cc2ccc(O)cc2)NC1=O]

a chemical formula of $C_{84}H_{137}N_{21}O_{20}$, and a molecular weight of 1761.15 kDa.

In the present disclosure, a stapled peptide whose i is 1 is named SAH-mAH2-4, which has an amino acid structure shown in formula IV:

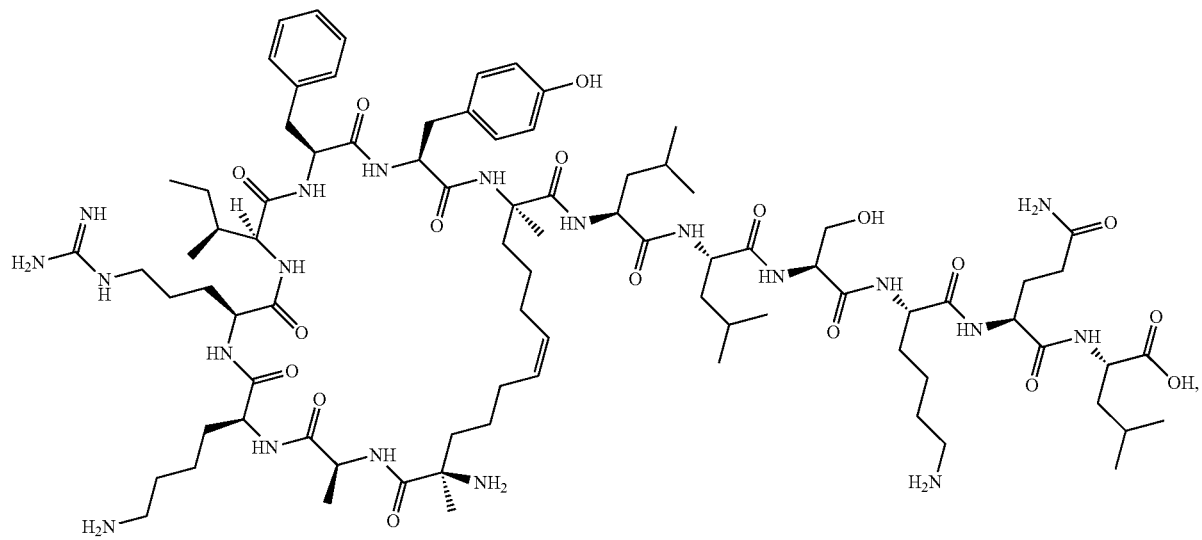 [SMILES: CC[C@H](C)[C@@H]1NC(=O)[C@H](CCCNC(=N)N)NC(=O)[C@H](CCCCN)NC(=O)[C@H](C)NC(=O)[C@](C)(N)CCC/C=C\CCC[C@](C)(C(=O)N[C@@H](CC(C)C)C(=O)N[C@@H](CC(C)C)C(=O)N[C@@H](CO)C(=O)N[C@@H](CCCCN)C(=O)N[C@@H](CCC(N)=O)C(=O)N[C@@H](CC(C)C)C(=O)O)NC(=O)[C@H](Cc2ccc(O)cc2)NC(=O)[C@H](Cc2ccccc2)NC1=O]

a chemical formula of $C_{85}H_{140}N_{20}O_{18}$, and a molecular weight of 1730.18 kDa.

In the present disclosure, a stapled peptide whose i is 6 is named SAH-mAH2-5, which has an amino acid structure shown in formula V:

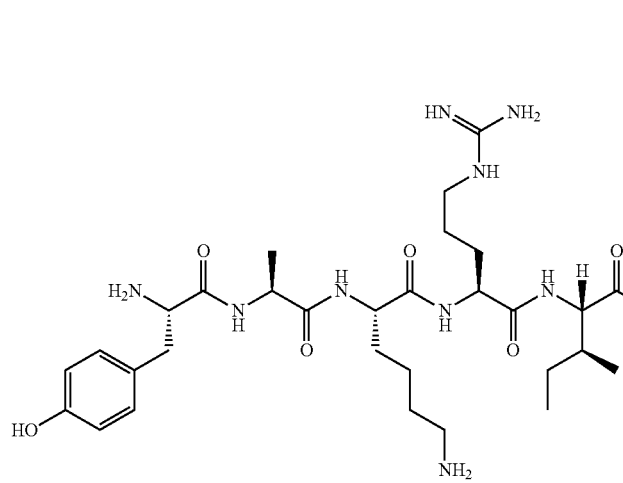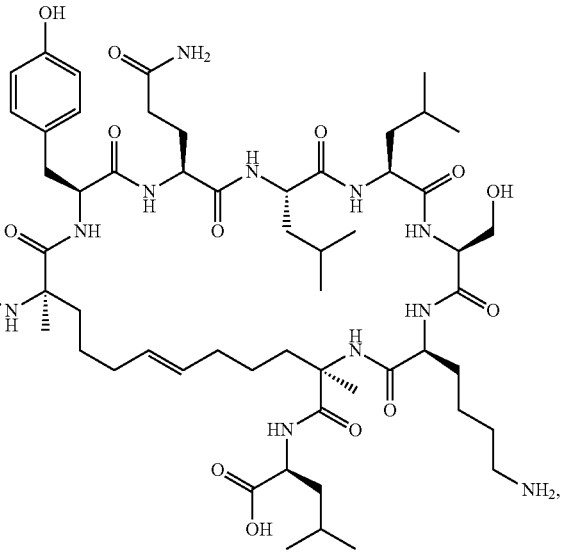

a chemical formula of $C_{85}H_{140}N_{20}O_{19}$, and a molecular weight of 1746.18 kDa.

In the present disclosure, SAHs are stapled α-helices; taking the SAH-mAH2-5 as an example, its chemical name is stapled α-helix-modified α-helix 2-5.

In the present disclosure, the mAH2 peptide is combined with two non-natural alkenyl amino acid units S5 at relative positions to form stapled SAH-mAH2-1 to SAH-mAH2-5; crosslinking by ring-closed olefin metathesis results in the formation of spiked peptides supported in an α-helical conformation. The SAH-mAH2-5 is a cell-permeable and reversible selective inhibitor for proteasomes, which can specifically inhibit the deubiquitination activity of USP10 and its interaction with N1ICD; while the remaining four peptides have not been further studied due to their weak affinity with ANK sequence. There is no special limitation on a source of the synthesized SAH-mAH2-1 to SAH-mAH2-5, and peptide synthesis methods well known in the art can be used. In the specific implementation, the stapled peptides each are purchased from Chinese Peptide Co., Ltd. (Hangzhou, China).

LINC00261 acts as an RNA decoy to inhibit c-myc-mediated glycolysis in pancreatic cancer. Furthermore, a previously-unrecognized functional polypeptide is identified and named Notch1 degradation-associated regulatory polypeptide for the first time, abbreviated as N1DARP. The polypeptide, encoded by LINC00261, is a novel tumor suppressor and chemosensitizer in pancreatic cancer; the N1DARP consists of 41 amino acids, with a specific amino acid sequence of: MVLLEKKRQYQGLCLLSPGYAKRI-FYQLLSKELYVDPIHID (SEQ ID NO: 2).

In the present disclosure, SAH-mAH2-1 to SAH-mAH2-5 each can bind to the ANK domain of Notch1 intracellular segment N1ICD, suggesting that the SAH-mAH2-1 to SAH-mAH2-5 each can inhibit the function of N1ICD. The SAH-mAH2-5 has the strongest binding ability (with a minimum dissociation constant of $8.98 \times 10)^{-10}$.

The present disclosure further provides use of the stapled peptide in preparation of a drug for treating pancreatic cancer.

In the present disclosure, the pancreatic cancer includes preferably LINC00261-deficient pancreatic cancer, N1DARP-deficient pancreatic cancer, or gemcitabine-resistant pancreatic cancer.

In the present disclosure, the SAH-mAH2-5 treats LINC00261-deficient pancreatic cancer, N1DARP-deficient pancreatic cancer, or gemcitabine (GEM)-resistant pancreatic cancer preferably by specifically inhibiting the deubiquitination activity of USP10. Specific inhibition of Notch signaling pathway by the stapled peptide SAH-mAH2-5 leads to persistent tumor regression of the LINC00261-deficient pancreatic cancer, N1DARP-deficient pancreatic cancer, or GEM-resistant pancreatic cancer in cell line- and pancreatic cancer patient-derived organoids as well as subcutaneous tumor-bearing mice, without affecting the liver, lungs, and kidneys and other major normal tissues and organs. The treatment response is positively related to the concentration of SAH-mAH2-5. SAH-mAH2-5-specific inhibition of USP10 results in persistent tumor regression through the N1ICD deubiquitination of USP10 and the dependent and independent regulation of Notch signaling pathway. Given that the SAH-mAH2-5 has been evaluated for preclinical efficacy, pharmacology, and safety on tumors in the human pancreatic cancer patient-derived organoids as well as subcutaneous tumor-bearing mice, its preclinical findings may also be applicable to human clinical use for patients.

The present disclosure further provides a drug for treating pancreatic cancer, including the stapled peptide as an active component, and a pharmaceutically acceptable auxiliary material.

In the present disclosure, the stapled peptide is the only active component of the drug.

In the present disclosure, a dosage form of the drug includes an injection.

The technical solutions of the present disclosure will be described below clearly and completely in conjunction with the examples of the present disclosure.

Example 1

Optimized Design, Synthesis, and Analysis of SAH-mAH Stapled Peptides

The SAH-mAH stapled peptides were shown in Table 1.

TABLE 1

| SAH peptide | Sequence |
|---|---|
| mAH2 | YAKRIFYQLLSKQL |
| SAH mAH2-1 | S5AKRS5FYQLLSKQL |
| SAH-mAH2-2 | YS5KRIS5YQLLSKQL |
| SAH-mAH2-3 | YAKRIS5YQLS5SKQL |
| SAH-mAH2-4 | S5AKRIFYS5LLSKQL |
| SAH-mAH2-5 | YAKRIS5YQLLSKS5L |

All peptides were produced by Chinese Peptide Co., Ltd. (Hangzhou, China). For in vitro and in vivo applications, the synthesized peptides were purified to a purity of greater than 98% by high-pressure liquid chromatography. An mAH2-5 peptide was combined with two non-natural alkenyl amino acid units S5 at relative positions to form a stapled peptide SAH-mAH2-5; crosslinking by ring-closed olefin metathesis resulted in the formation of spiked peptides supported in an α-helical conformation. During in vitro experiments, the peptides were dissolved in the PBS to generate a 4 mM stock solution. For in vivo use, the peptides were dissolved in the PBS and kept on ice prior to injection. The solution was placed at a room temperature prior to injection.

Surface plasmon resonance (SPR) analysis was conducted with a BIAcore T200 instrument (GE Healthcare, Pittsburgh, USA) to analyze the binding kinetics between N1DARP or SAH-mAH2-5 and a monitor peptide. Dissociation constants (KD) were calculated according to BIA evaluation software.

Figure 1B:
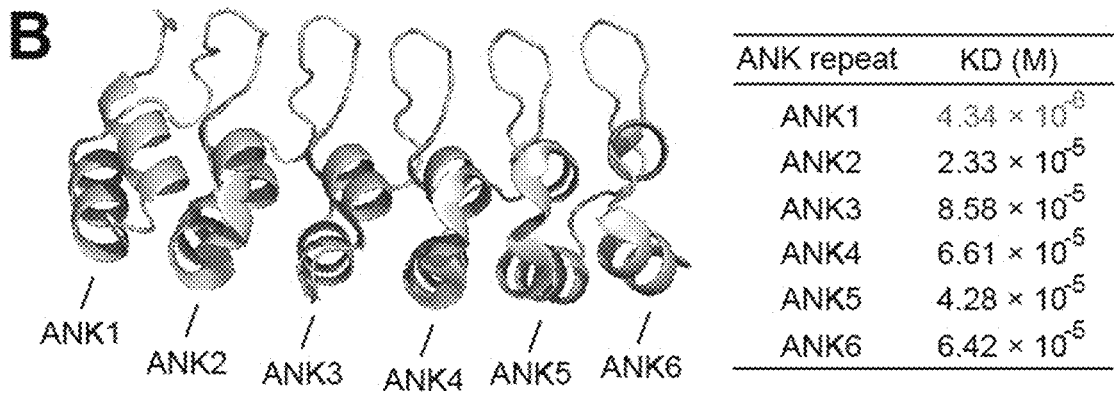
Figure 1E:
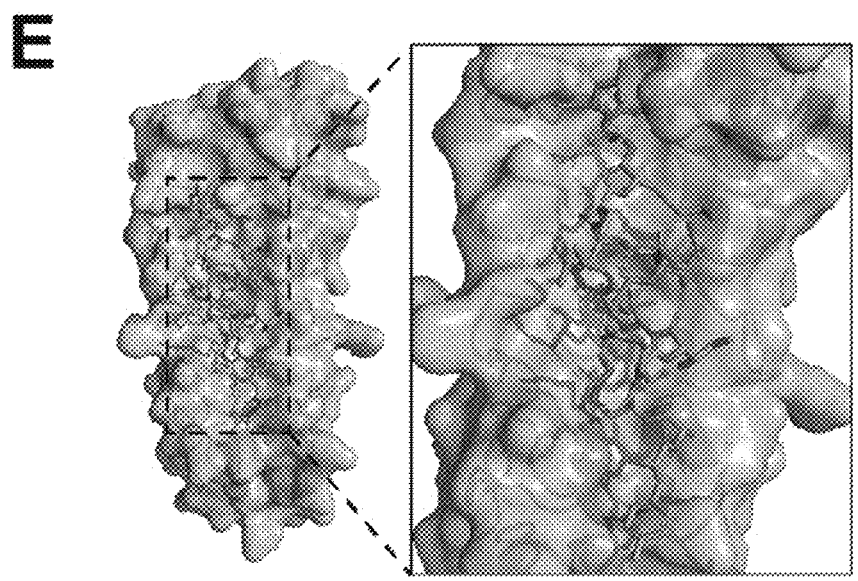

A tertiary structure simulating the N1DARP was analyzed online using I-TASSAR, a hierarchical server for protein structure prediction, and two α-helical peptides (AH1 and AH2) were identified (FIG. 1A, left side). SPR analysis showed that the purified AH2 peptide had higher affinity to the ANK domain (FIG. 1A, right side). A tertiary structure of the ANK domain of N1ICD was obtained from a PDB database, where an α-helix secondary structure of ANK ranged from ANK1 to ANK6; the SPR analysis indicated that AH2 readily interacted with ANK1 (FIG. 1B to FIG. 1D). In order to optimize the physicochemical properties of AH2, the amino acid sequence was checked, and it was found that a negatively-charged amino acid Glu32 might affect the permeability of AH2 to cancer cells, such that an attempt was made to replace this amino acid. SPR analysis showed comparable affinity for ANK between AH2 and modified AH2, and the modified AH2 was designated as mAH2 (FIG. 1C). Furthermore, in order to identify the essential amino acids that mediated the interaction between mAH2 and ANK, amino acid substitutions were conducted for each amino acid of mAH2 substituted with Ala, which were then subjected to SPR analysis. The results showed that Tyr26, Leu28, and Leu33 were essential amino acids for the interaction between mAH2 and ANK. Based on the above evidence, mAH2 was then further modified by inserting molecular staples at 5 positions and denoted as stapled α-helices (SAHs). SPR analysis indicated that the SAH-mAH2-5 had the highest affinity for ANK (FIG. 1D). Molecular docking using CABS-dock demonstrated that the SAH-mAH2-5 interacted with ANK by intercalating into surface grooves of the ANK via electrostatic attraction and hydrogen bonding (FIG. 1E).

To examine the physicochemical stability of SAH-mAH2-5, mAH2, Pep2-mAH2, and SAH-mAH2-5 were incubated with proteinase K, pepsin, and mouse plasma. It was found that SAH-mAH2-5 significantly enhanced the resistance to proteases, and prolonged the half-life in plasma, indicating that the SAH-mAH2-5 had a remarkable physicochemical stability.

Example 2

Study on Tumor Suppressor Effect and GEM Sensitization of SAH-mAH2-5 Stapled Peptides Four pancreatic cancer tissues were obtained from Ruijin Hospital Affiliated to Shanghai Jiaotong University School of Medicine for organoid culture. All enrolled patients met the following criteria: (i) pathologically diagnosed with pancreatic cancer; (ii) with relatively complete clinicopathological and follow-up data; (iii) without preoperative chemotherapy. Written informed consent was obtained from all relevant patients for the trial, and the study protocol was approved by the Ethics Committee of Ruijin Hospital.

Establishment of patient-derived pancreatic cancer organoids: the normal pancreatic tissues were excised, remaining pancreatic cancer tissues were minced, and enzymatically digested with collagenase (1 mg/ml to 2 mg/ml; Sigma-Aldrich, C9407) in a water bath at 37° C. for 1 h to 2 h. A resulting suspension was filtered through a 100 μm filter to retain tissue debris. The tissue debris was centrifuged at 530 g for 5 min to obtain organoid fractions and resuspended in an RPMI 1640 medium; a resulting suspension was mixed with a cold Matrigel (BD Biocoat, 356234, 10 mg/ml) and then solidified on a pre-warmed 24-well suspension plate at 37° C. for 20 min. After complete gelation, 400 ml of an organoid medium was added to each well, and the plate was transferred to a 37° C./5% humidified $CO_2$ incubator with 2% or ambient $O_2$. The medium was changed every 4 d and the organoids were passaged every 1 to 4 weeks.

All animal experimental procedures met institutional ethical requirements and were approved by the Animal Use and Care Committee of Shanghai Jiaotong University School of Medicine. Nude BALB/c mice (male, 4 to 6 weeks old) were purchased from the Chinese Academy of Sciences (Shanghai, China) and kept in a specific pathogen-free facility. For a subcutaneously-injected tumor model, the pancreatic cancer patient-derived organoids ($5\times10^6$ cells/site) were injected subcutaneously into the right side of each mouse. From the first injection, a tumor volume was measured every 7 d using the formula: tumor volume $(mm^3)=\frac{1}{2}(a\times b^2)$, where "a" represented the longest longitudinal diameter and "b" represented the longest transverse diameter.

To evaluate the efficacy of SAH-mAH2-5 in vivo, Capan1 cells ($1\times10^7$ cells/site) and four organoids ($5\times10^6$ cells/site) were subcutaneously injected. One week after inoculation, SAH-CTRL/SAH-mAH2-5 (1/2/3/4/5 mg/kg) and GEM (50 mg/kg) were intravenously injected weekly at the indicated concentrations. Within 35 d from the first injection, the tumor volume was measured every 7 d, and the formula was: tumor volume (mm$^3$)=½(a×b$^2$).

To evaluate the influence of SAH-mAH2-5 on improved survival of tumor-bearing mice, luciferase-labeled Capan1 cells (5.0×10$^5$) and four organoids (1.0×10$^5$) were mixed with the Matrigel and then inoculated into the pancreas of each mouse, thereby establishing an orthotopic implantation model of the pancreas. One week after inoculation, the SAH-CTRL/SAH-mAH2-5 (1/2/3/4/5 mg/kg) was intravenously injected weekly at the indicated concentrations. After weekly inoculations, the development of Capan1 cells and organoids in peptide-treated BALB/c nude mice was monitored in vivo by an IVIS spectroscopic optical imaging system.

Figure 2A:
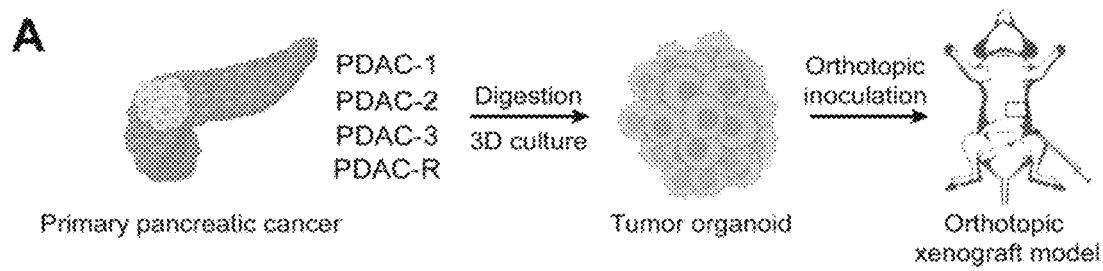
FIG. 2A-M show that the SAH-mAH2-5 inhibits pancreatic cancer progression and enhances its sensitivity to GEM chemotherapy in pancreatic cancer patient tissue-derived organoids (PDOs) and PDO nude mouse orthotopic xenograft models (PDOXs); where
Figure 2B:
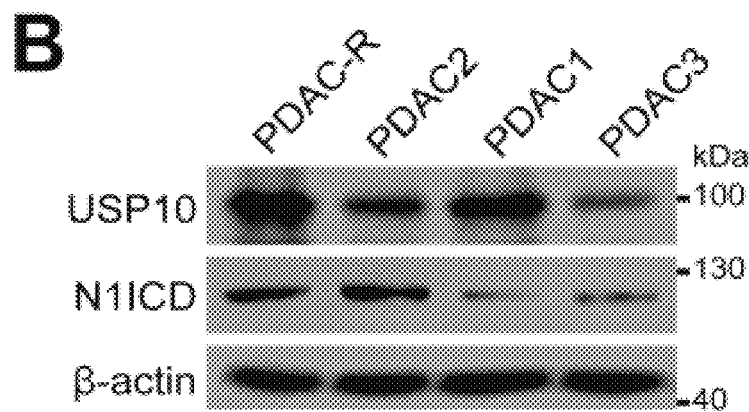
Figure 2C:
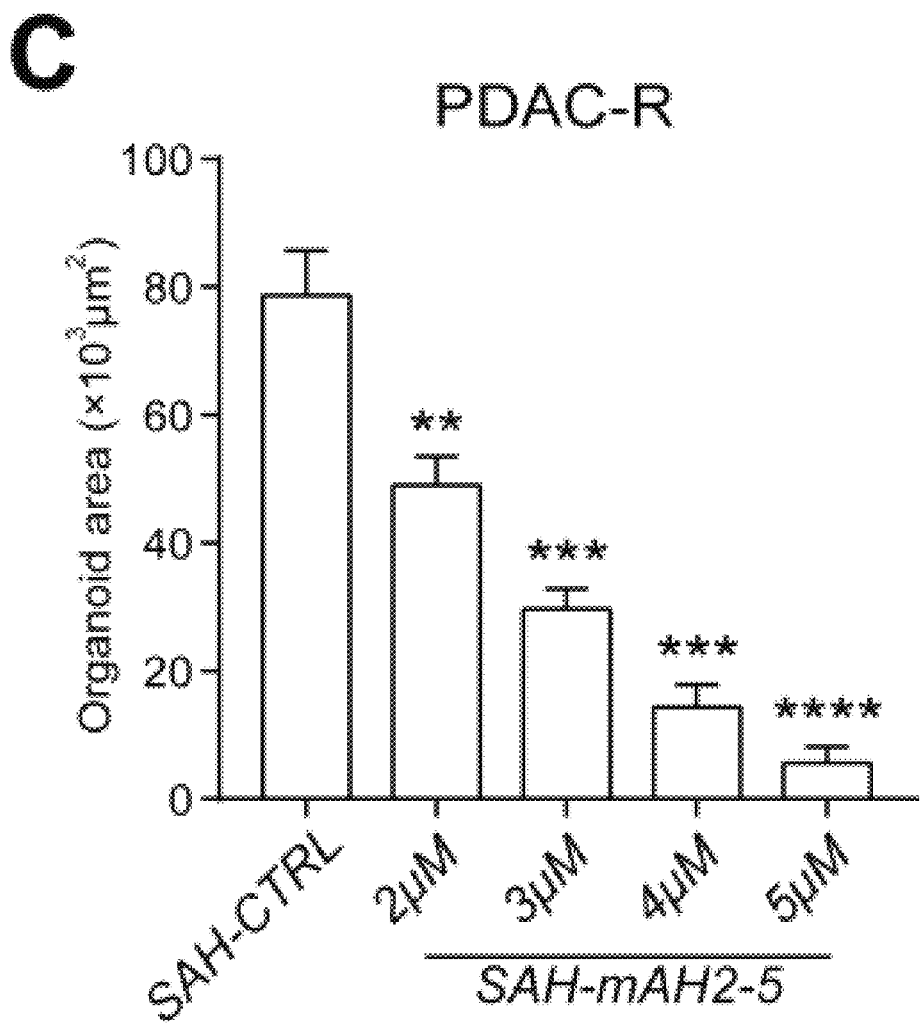
Figure 2D:
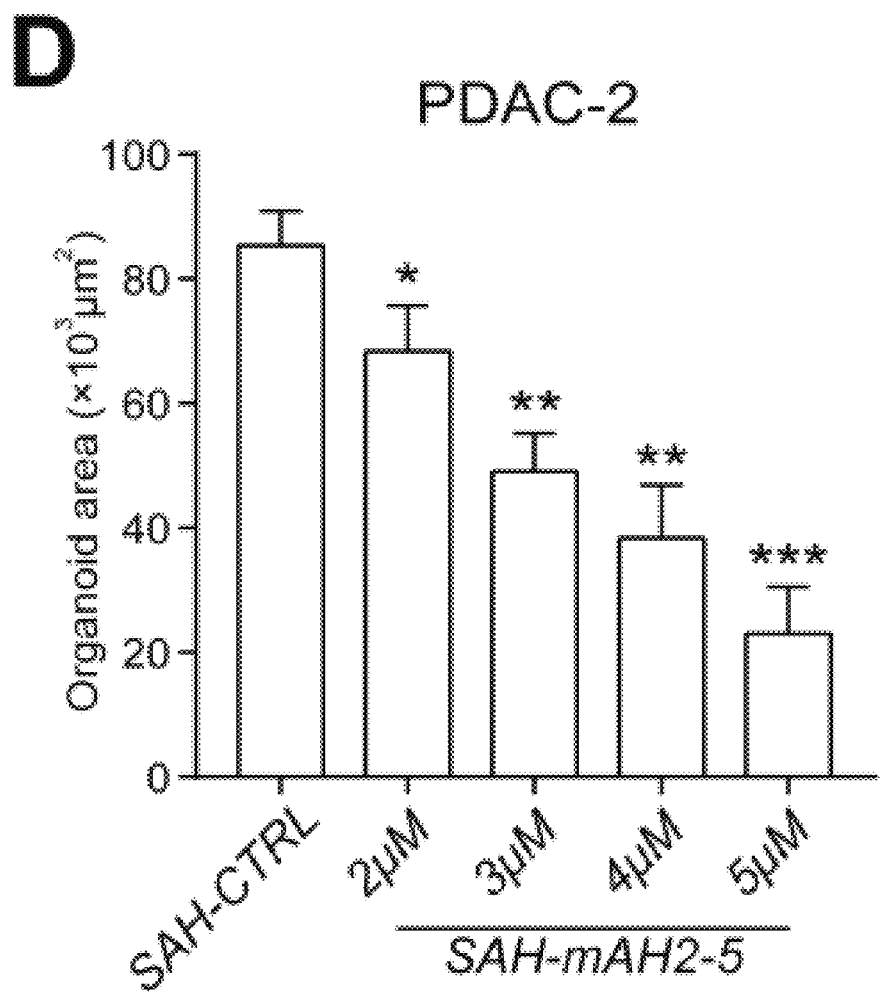
Figure 2E:
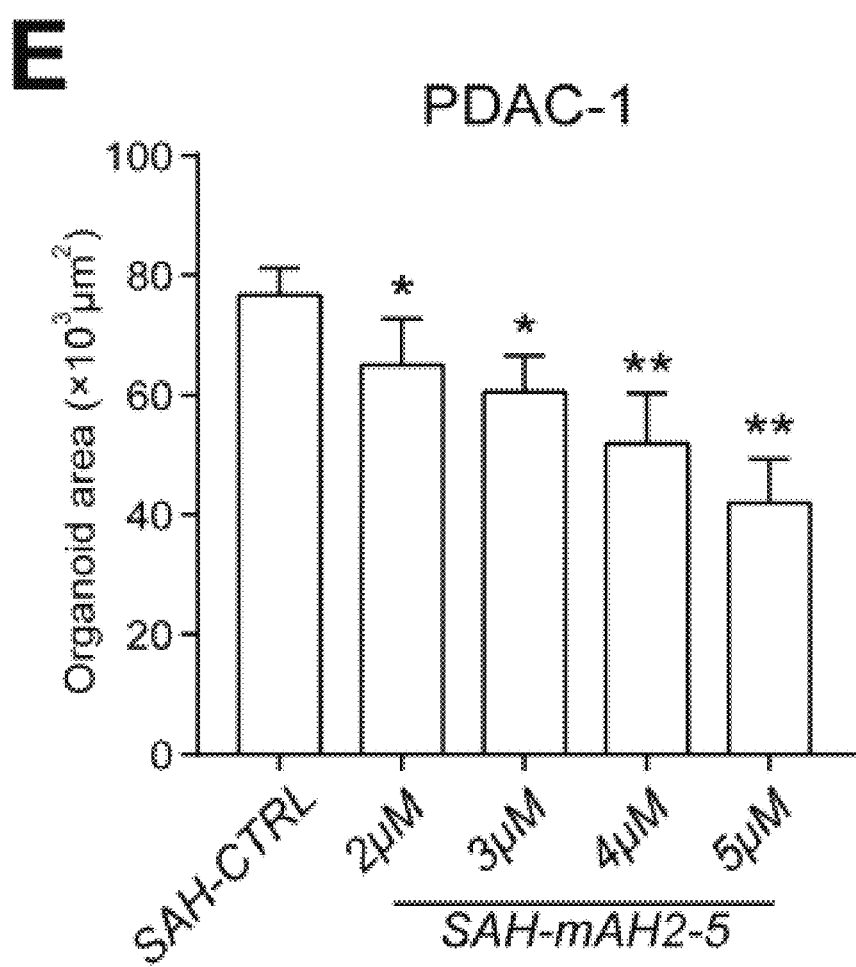
Figure 2F:
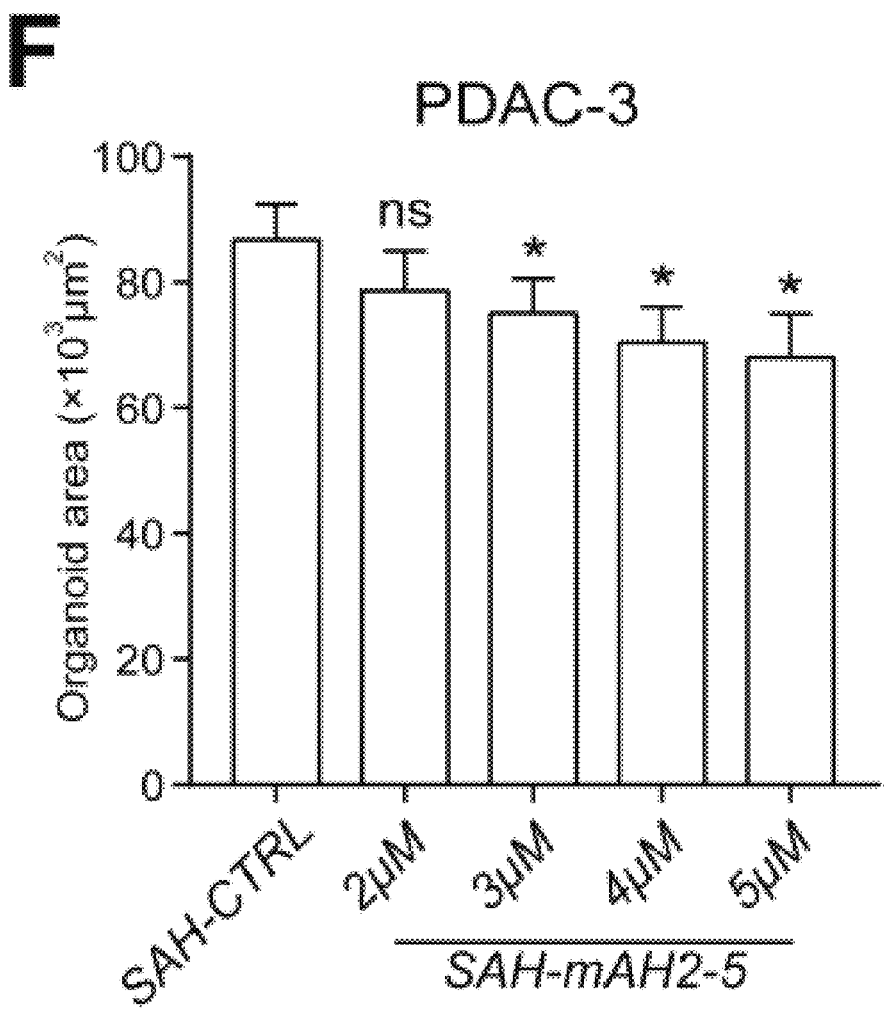
Figure 2G:
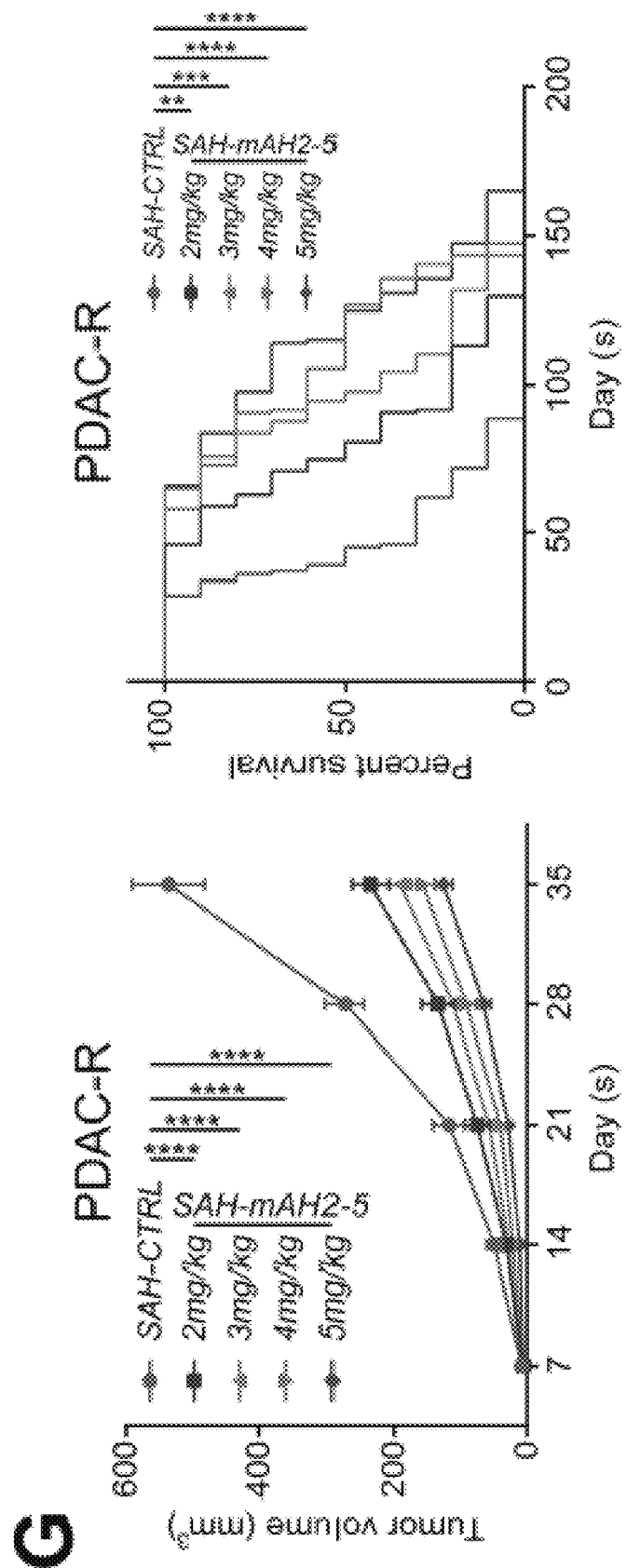
Figure 2H:
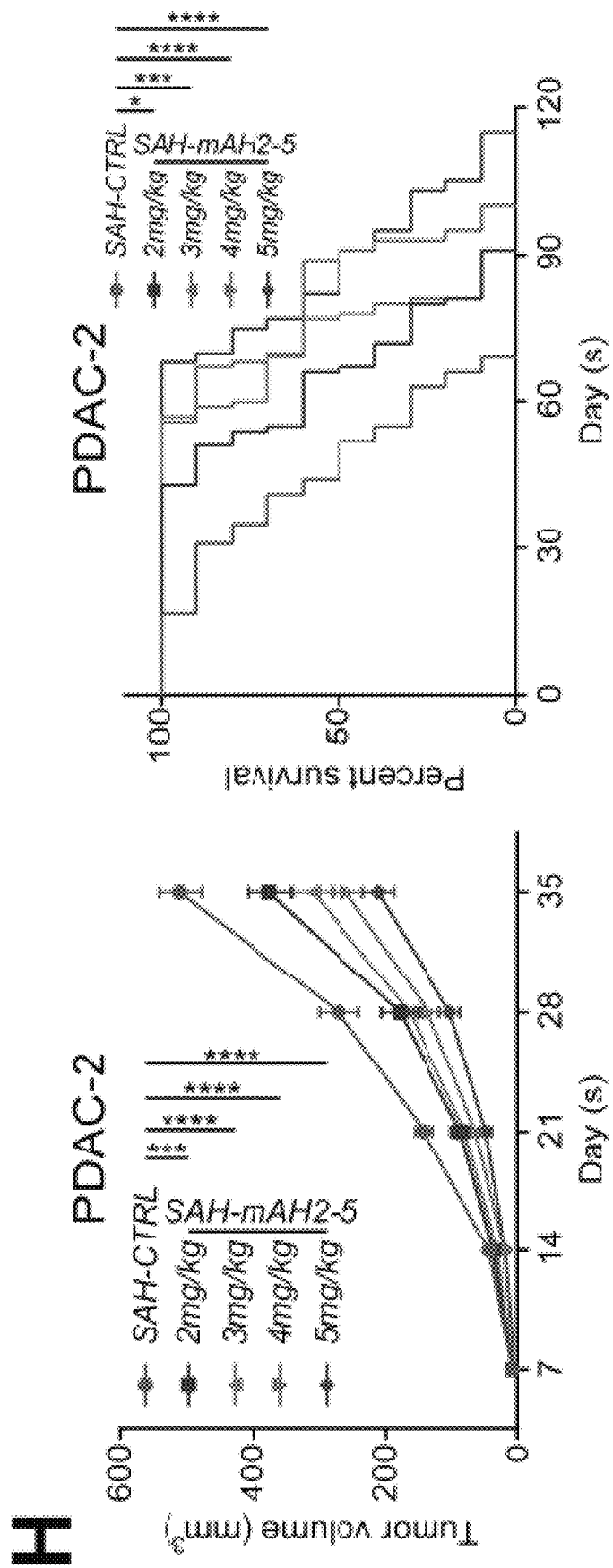
Figure 2I:
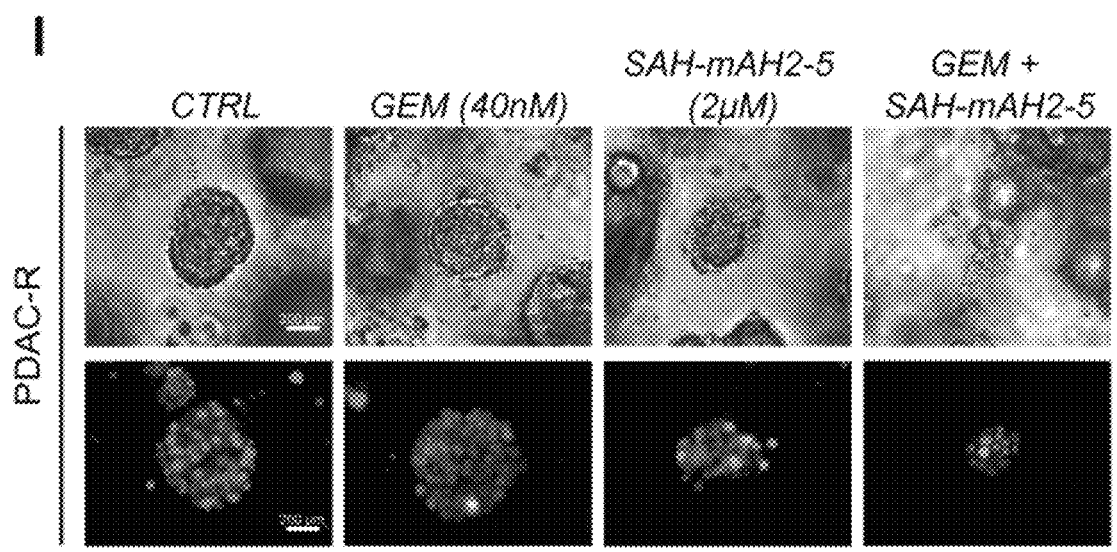
Figure 2J:
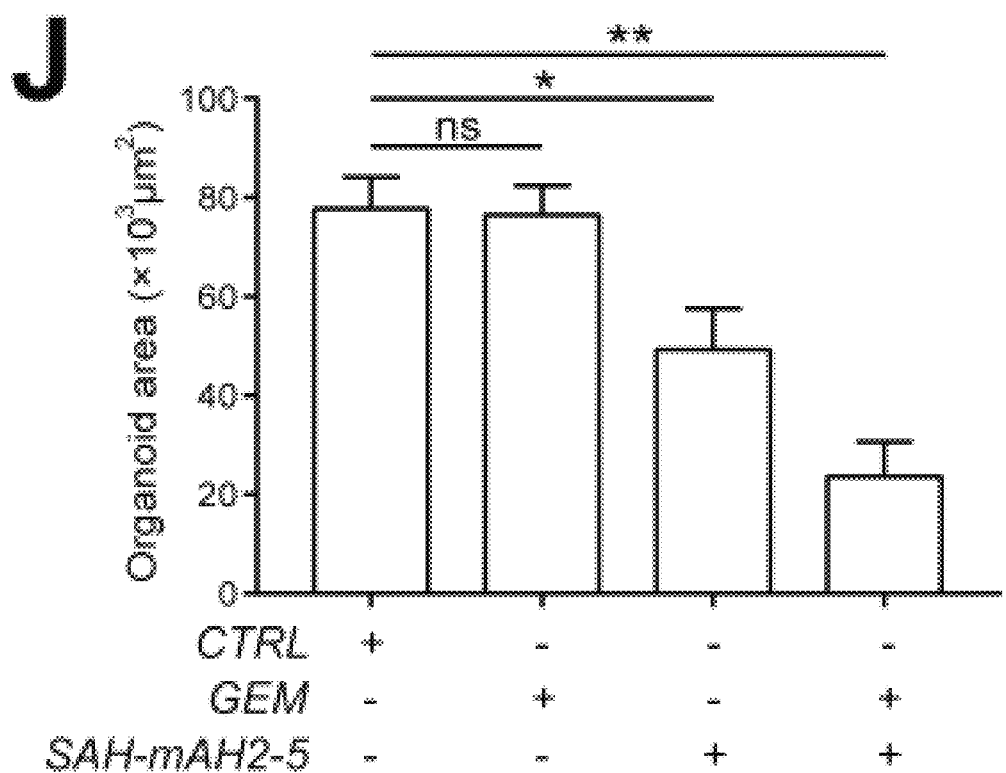
Figure 2K:
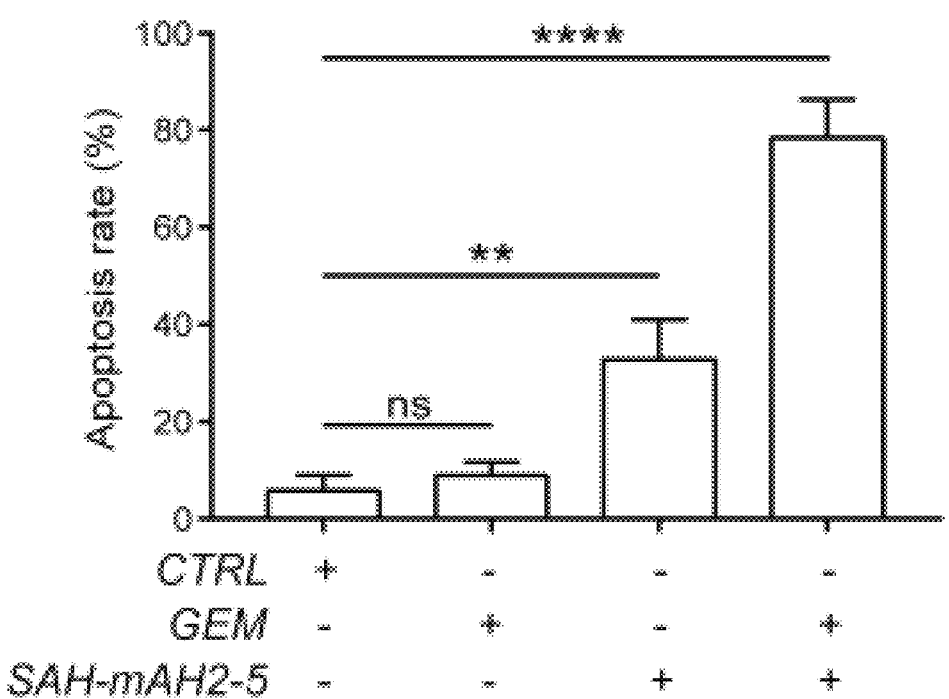
Figure 2L:
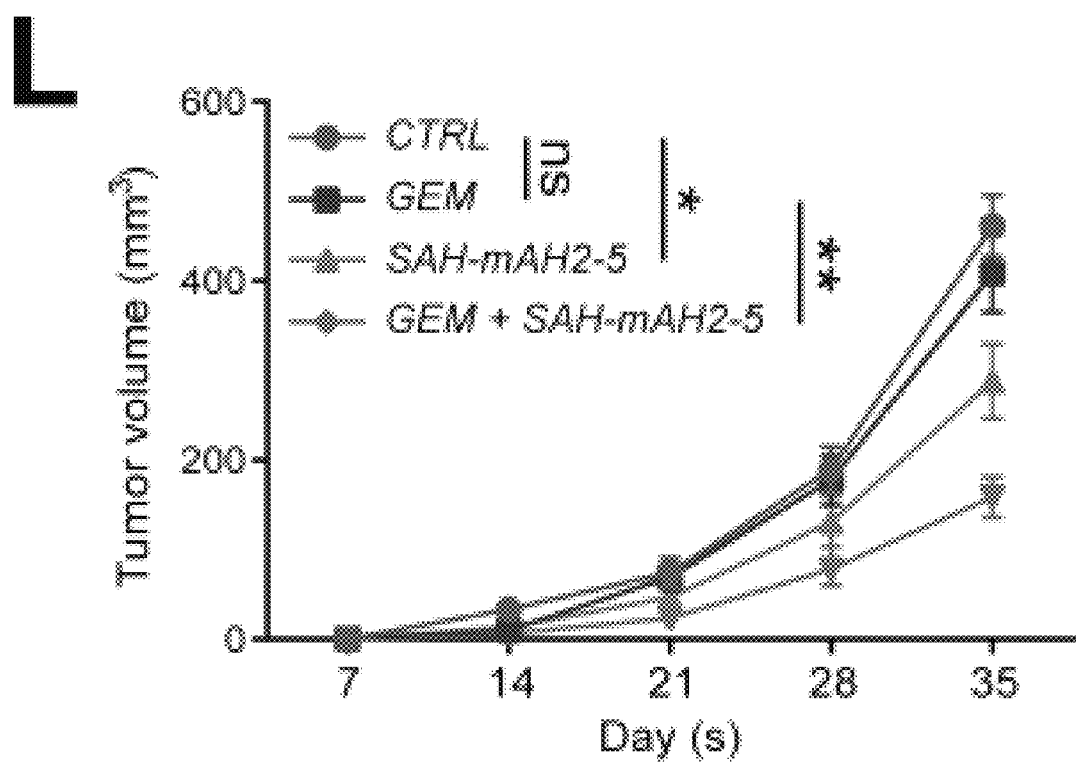
Figure 2M:
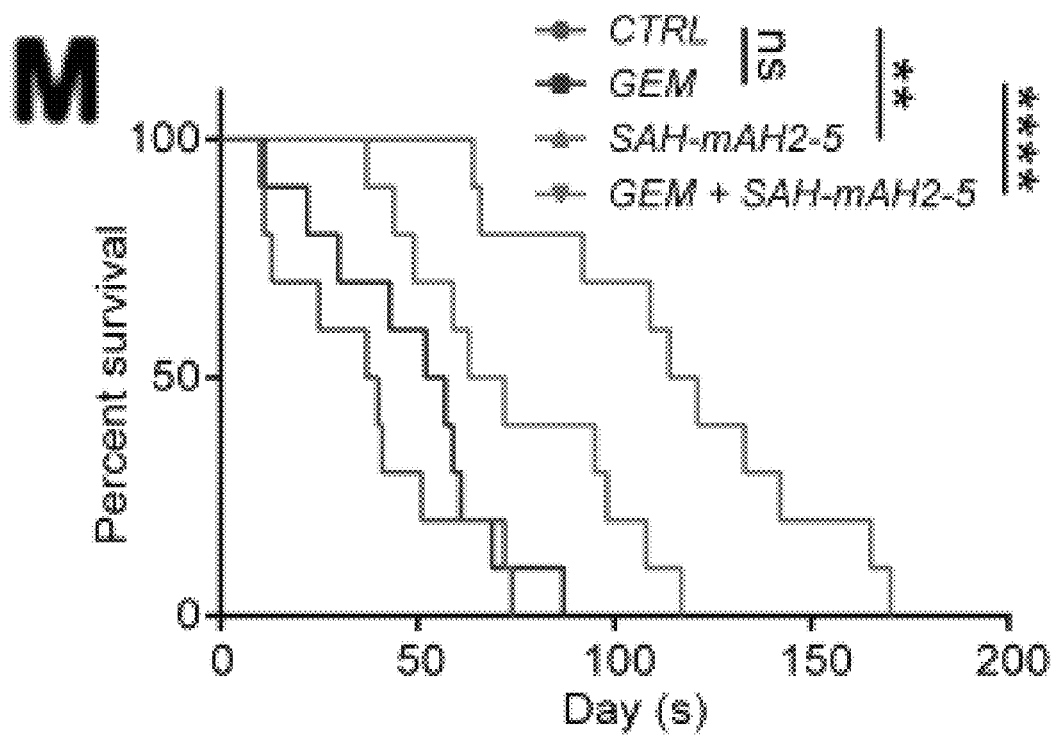

In the orthotopic PDOX model of PDAC with high USP10 and N1ICD expression levels (FIG. 2A and FIG. 2B), SAH-mAH2-5 showed significant organoid growth inhibition (FIG. 2C to FIG. 2E), as well as subcutaneous inhibition of tumor regression in nude mice and prolonged median survival (FIG. 2G and FIG. 2H). However, in the PDAC-1 and PDAC-3 models with relatively low USP10 and N1ICD expression levels, there was a poor inhibition effect, suggesting that the tumor suppressor effect of SAH-mAH2-5 was indeed related to the expression of USP10 and N1ICD. Additionally, tumors injected with the combination of SAH-mAH2-5 and GEM had smaller organoids (FIG. 2I), slower growth progression (FIG. 2J), and a greater number of cells undergoing apoptosis (FIG. 2K) compared with the control; meanwhile, the tumor-bearing mice had smaller tumors (FIG. 2L) and longer survival (FIG. 2M). In summary, these data suggested that the novel stapled peptide SAH-mAH2-5 targeting the USP10-N1DARP-N1ICD pathway might be a promising strategy for the treatment of pancreatic cancer.

Example 3

Analysis of SAH-mAH2-5 Simulating LINC00261/N1DARP to Interfere with N1ICD-USP10 Interaction and to Inhibit USP10 Deubiquitination Activity The pancreatic cancer cell line Capan1 was purchased from the Cell Bank of the Chinese Academy of Sciences. The cells were STR-identified, negative for mycoplasma, and cultured in the RPMI 1640 supplemented with 10% fetal bovine serum and antibiotics.

A RIPA buffer was mixed with a cocktail of proteases and phosphatase inhibitors for lysing cell samples. Proteins were separated by 10% SDS-PAGE and transferred to a PVDF membrane. The images were generated by a Tanon 5200 chemiluminescence imaging system (Shanghai Tanon Life Science Instrument Co., Ltd.). The corresponding proteins were detected with primary antibodies and appropriate secondary antibodies. The primary antibodies were as follows: anti-USP10 (CST, #8501, 1:1000 for WB, 1:200 for IP), anti-β-actin (CST, #3700, 1:1000 for WB), and anti-N1ICD (CST, #4147, 1:1000 for WB, 1:200 for IP).

Immunoprecipitation analysis: pancreatic cancer cells transfected with indicated plasmid or lentivirus were collected and lysed for 10 min on ice. A resulting lysate was centrifuged to obtain a supernatant, which was then incubated with appropriate antibodies and protein A/G+agarose (Santa Cruz Biotechnology) overnight at 4° C. A resulting immune complex was washed 4 to 6 times and boiled in a 2×SDS sample buffer for 5 min. A resulting product was separated and co-precipitated using SDS-PAGE and blotted with specific antibodies. A resulting binding protein was dissolved in the SDS sample buffer and analyzed by immunoblotting.

Figure 3A:
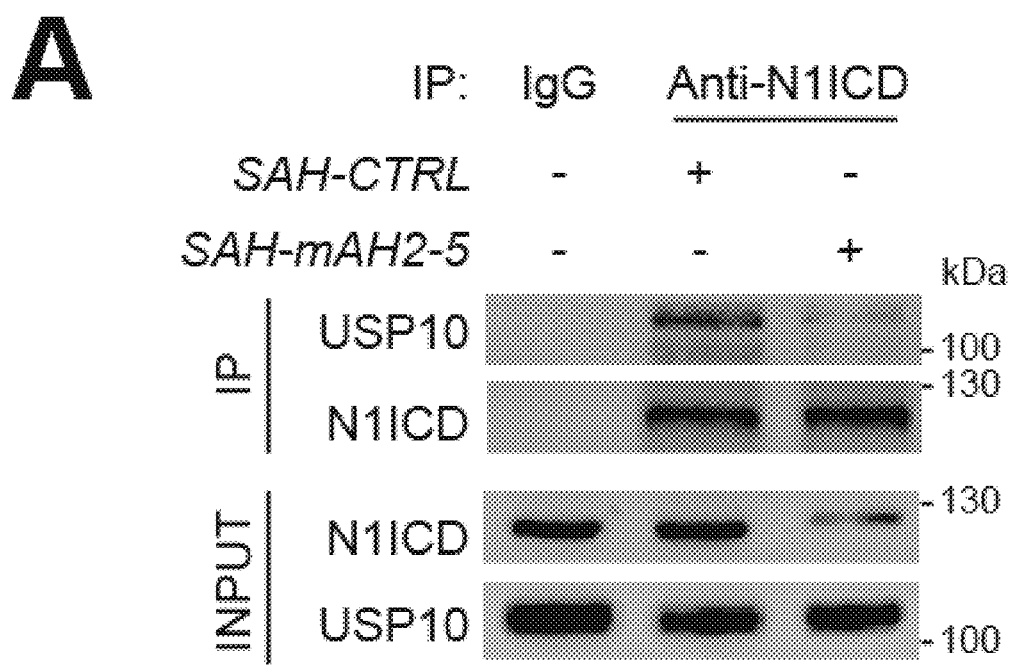
FIG. 3A-C show results of a dependent mechanism of the SAH-mAH2-5 on regulation of Notch signaling pathway by USP10; where
Figure 3B:
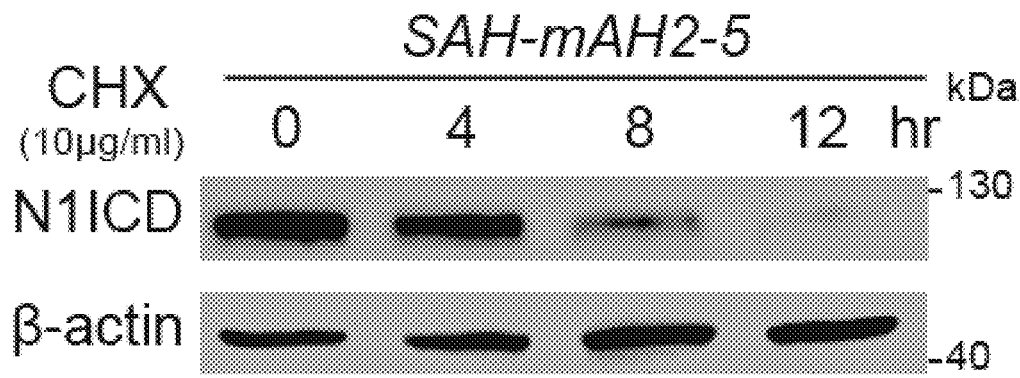
Figure 3C:
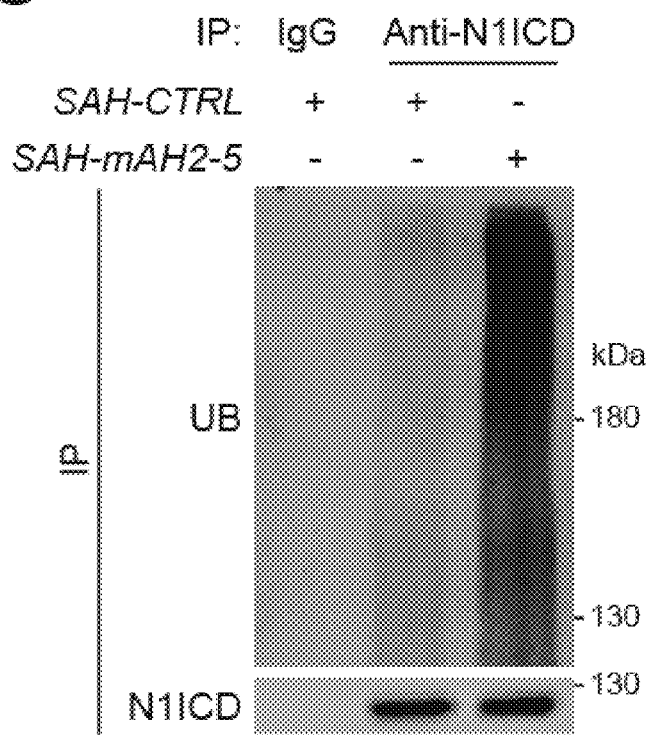

Treatment of Capan1 cells with SAH-mAH2-5 confirmed that the SAH-mAH2-5 could inhibit USP10-N1ICD interaction (FIG. 3A), inhibiting Notch signaling and its N1ICD expression in a time- and dose-dependent manner (FIG. 3B). The SAH-mAH2-5 inhibited N1ICD stability (FIG. 3B) and deubiquitination (FIG. 3C) by counteracting the USP10-N1ICD interaction. These data suggested that by simulating N1DARP function, the SAH-mAH2-5 inhibited USP10-N1ICD interaction and USP10 deubiquitination, inhibited occurrence of pancreatic cancer, and restored drug sensitivity to GEM.

Example 4

Evaluation of In Vivo Safety of SAH-mAH Stapled Peptides in Mice

To roughly assess the toxicity of SAH-mAH2-5, healthy BALB/c nude mice (5 weeks) were intravenously injected with SAH-CTRL or SAH-mAH2-5 (2 mg/kg) weekly for 4 weeks. The mice were sacrificed, and organs such as pancreas, lung, spleen, kidney, liver, and colon were extracted, which were then subjected to HE staining to screen morphological abnormalities. In addition, serum was collected for biochemical analysis of alanine aminotransferase (ALT), aspartate aminotransferase (AST), blood urea nitrogen (BUN), and creatinine (CR) by a chemical analyzer TBA-40FR (Toshiba Medical Systems, Japan).

Figure 4A:
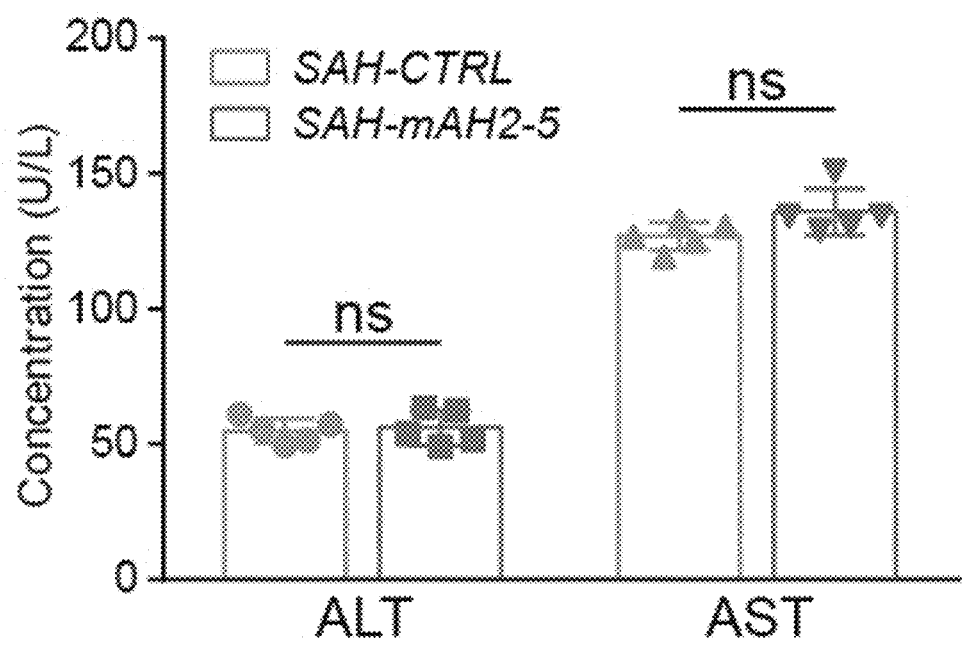
FIG. 4A-C shows results of serology and major organ influences in SAH-mAH2-5-treated mice; where
Figure 4B:
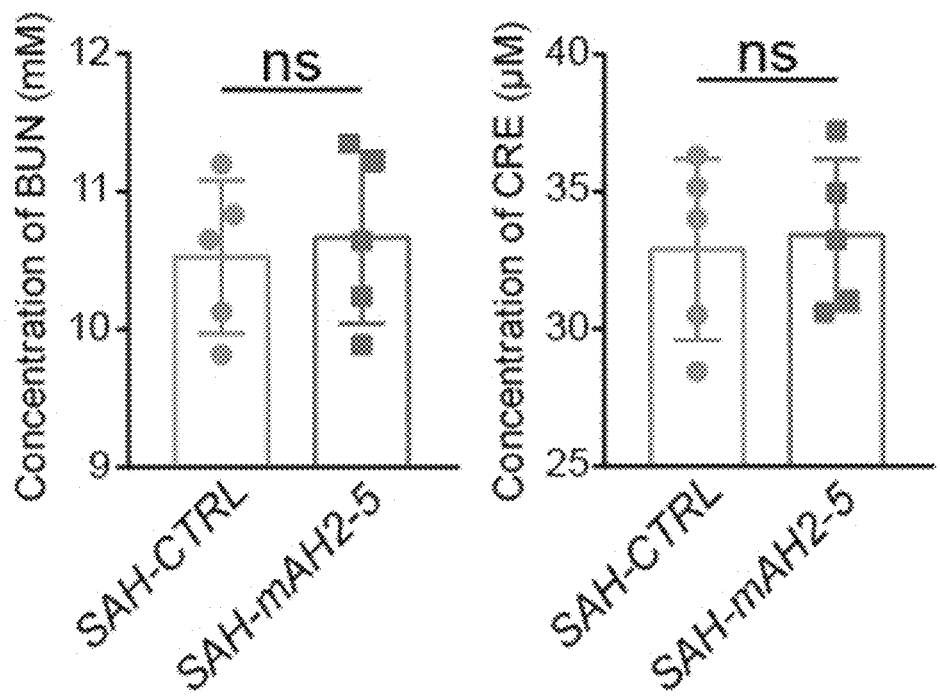
Figure 4C:
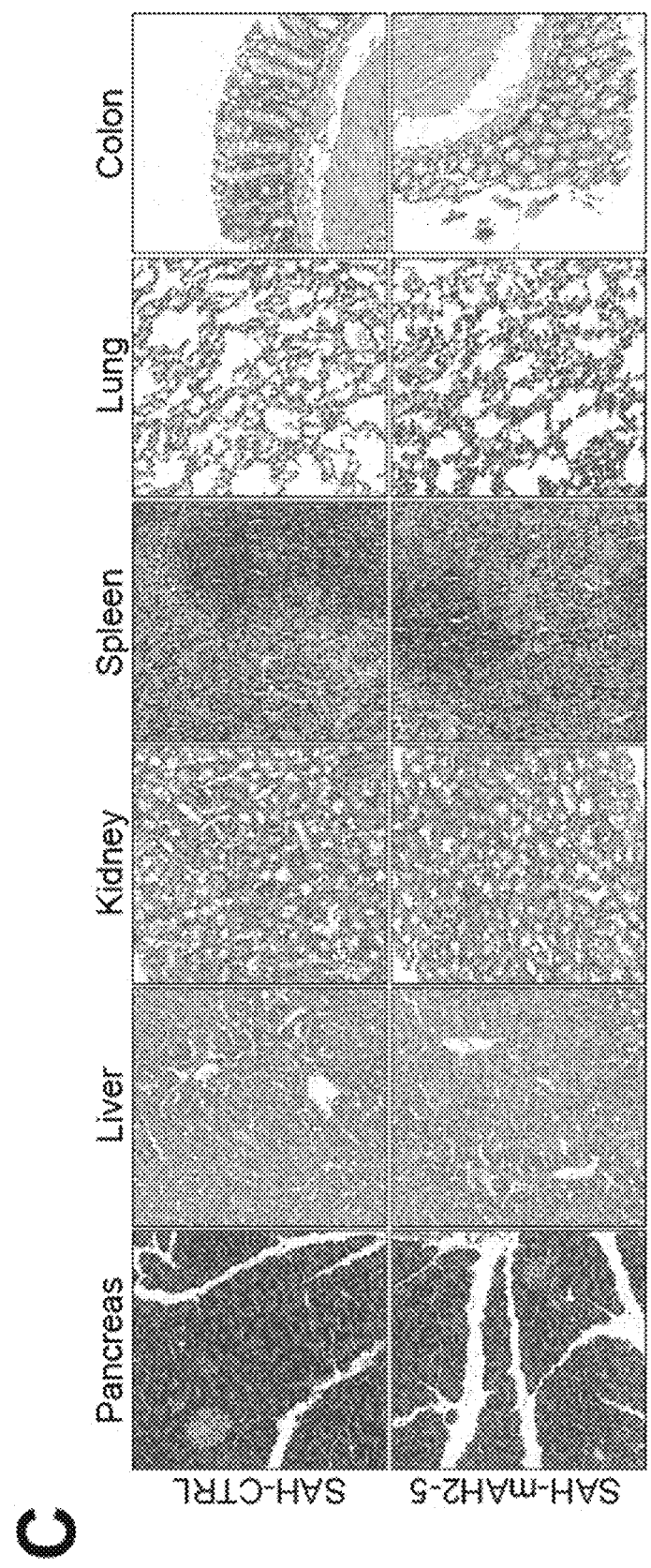

Serum examination of SAH-mAH2-5-injected mice showed no abnormalities in the main indicators of liver and kidney functions (FIG. 4A and FIG. 4B). Immunohistochemical analysis also showed no morphological changes in major functional organs such as pancreas, liver, kidney, spleen, lung, and large intestine (FIG. 4C), indicating that SAH-mAH2-5 had almost no toxic effect. Accordingly, this stapled peptide might be a promising Notch signaling inhibitor, especially for N1ICD, which is used for clinical drug therapy of pancreatic cancer.

Although the above example has described the present disclosure in detail, it is only a part of, not all of, the examples of the present disclosure. Other examples may also be obtained by persons based on the example without creative efforts, and all of these examples shall fall within the protection scope of the present disclosure.

What is claimed is:

1. A stapled peptide, prepared by using a linear peptide with an amino acid sequence shown in SEQ ID NO: 1 as a peptide chain template, and replacing i-th and (i+7)-th amino acids of the linear peptide with S5 separately and conducting cyclization; alternatively, replacing n-th and (n+4)-th amino acids of the linear peptide with S5 separately and conducting cyclization; wherein
S5 is 2-amino-2-methyl-6-heptenoic acid; i is a positive integer of less than or equal to 7, and n is a positive integer of less than or equal to 10.

2. The stapled peptide according to claim 1, wherein i is 1 or 6.

3. The stapled peptide according to claim 1, wherein n is 1, 2, or 6.

4. A method for treating pancreatic cancer, wherein administering the stapled peptide according to claim 1 to a subject in demand.

5. The method according to claim 4, wherein i is 1 or 6.

6. The method according to claim 4, wherein n is 1, 2, or 6.

7. The method according to claim 4, wherein the pancreatic cancer comprises LINC00261-deficient pancreatic cancer, N1DARP-deficient pancreatic cancer, or gemcitabine-resistant pancreatic cancer.

8. The method according to claim 5, wherein the pancreatic cancer comprises LINC00261-deficient pancreatic cancer, N1DARP-deficient pancreatic cancer, or gemcitabine-resistant pancreatic cancer.

9. The method according to claim 6, wherein the pancreatic cancer comprises LINC00261-deficient pancreatic cancer, N1DARP-deficient pancreatic cancer, or gemcitabine-resistant pancreatic cancer.

10. A drug for treating pancreatic cancer, comprising the stapled peptide according to claim 1 as an active component, and a pharmaceutically acceptable auxiliary material.

11. The drug according to claim 10, wherein i is 1 or 6.

12. The drug according to claim 10, wherein n is 1, 2, or 6.

13. The drug according to claim 10, wherein the stapled peptide is the only active component of the drug.

14. The drug according to claim 11, wherein the stapled peptide is the only active component of the drug.

15. The drug according to claim 12, wherein the stapled peptide is the only active component of the drug.

16. The drug according to claim 10, wherein a dosage form of the drug comprises an injection.

17. The drug according to claim 11, wherein a dosage form of the drug comprises an injection.

18. The drug according to claim 12, wherein a dosage form of the drug comprises an injection.

19. The drug according to claim 13, wherein a dosage form of the drug comprises an injection.

20. The drug according to claim 14, wherein a dosage form of the drug comprises an injection.

* * * * *